US008268897B2

(12) United States Patent
Huffman

(10) Patent No.: US 8,268,897 B2
(45) Date of Patent: Sep. 18, 2012

(54) INCORPORATION OF CATALYTIC DEHYDROGENATION INTO FISCHER-TROPSCH SYNTHESIS TO LOWER CARBON DIOXIDE EMISSIONS

(75) Inventor: Gerald P. Huffman, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 206 days.

(21) Appl. No.: 12/790,353

(22) Filed: May 28, 2010

(65) Prior Publication Data
US 2011/0294906 A1 Dec. 1, 2011

(51) Int. Cl.
  *C07C 27/00* (2006.01)
(52) U.S. Cl. ........ 518/700; 518/702; 518/703; 518/705; 518/714; 518/715
(58) Field of Classification Search .................. 518/700, 518/702, 703, 705, 714, 715
See application file for complete search history.

(56) References Cited

U.S. PATENT DOCUMENTS

| 5,834,522 A | 11/1998 | Mignard et al. |
| 6,392,109 B1 | 5/2002 | O'Rear et al. |
| 6,432,866 B1 | 8/2002 | Tennent et al. |
| 6,713,519 B2 | 3/2004 | Wang et al. |
| 6,872,753 B2 | 3/2005 | Landis et al. |
| 6,875,417 B1 | 4/2005 | Shah et al. |
| 6,903,139 B2 | 6/2005 | Landis et al. |
| 6,919,062 B1 | 7/2005 | Vasileiadis et al. |
| 6,958,363 B2 | 10/2005 | Espinoza et al. |
| 7,012,102 B2 | 3/2006 | Font Freide et al. |
| 7,057,081 B2 | 6/2006 | Allison et al. |
| 7,332,147 B2 | 2/2008 | Takahashi et al. |
| 7,375,142 B2 | 5/2008 | Pearson |

*Primary Examiner* — Jafar Parsa
(74) *Attorney, Agent, or Firm* — King & Schickli, PLLC

(57) ABSTRACT

A method for producing liquid fuels includes the steps of gasifying a starting material selected from a group consisting of coal, biomass, carbon nanotubes and mixtures thereof to produce a syngas, subjecting that syngas to Fischer-Tropsch synthesis (FTS) to produce a hyrdrocarbon product stream, separating that hydrocarbon product stream into C1-C4 hydrocarbons and C5+ hydrocarbons to be used as liquid fuels and subjecting the C1-C4 hydrocarbons to catalytic dehydrogenation (CDH) to produce hydrogen and carbon nanotubes. The hydrogen produced by CDH is recycled to be mixed with the syngas incident to the FTS reactor in order to raise the hydrogen to carbon monoxide ratio of the syngas to values of 2 or higher, which is required to produce liquid hydrocarbon fuels. This is accomplished with little or no production of carbon dioxide, a greenhouse gas. The carbon is captured in the form of a potentially valuable by-product, multi-walled carbon nanotubes (MWNT), while huge emissions of carbon dioxide are avoided and very large quantities of water employed for the water-gas shift in traditional FTS systems are saved.

11 Claims, 2 Drawing Sheets

INCORPORATION OF CATALYTIC
DEHYDROGENATION INTO
FISCHER-TROPSCH SYNTHESIS TO LOWER
CARBON DIOXIDE EMISSIONS

This invention was made with government support under contract DE-FC26-05NT42456 awarded by U.S. Department of Energy. The government has certain rights in the invention.

TECHNICAL FIELD

The present invention relates generally to the production of synthetic fuels and, more particularly, to a modified and improved Fischer-Tropsch reaction that more economically produces useful synthetic hydrocarbon fuels while advantageously reducing carbon dioxide by-products of the Fischer-Tropsch synthesis process.

BACKGROUND OF THE INVENTION

The Fischer-Tropsch synthesis (FTS) is a process by which synthetic gas or syngas, comprising carbon monoxide and hydrogen, is converted into liquid hydrocarbon fuels like synthetic diesel and jet fuel. Prior to the FTS process, the coal, gas or biomass feed stocks are gasified using intense heat and pressure in order to produce the syngas for the FTS process. The synthetic fuels resulting from the FTS process advantageously increase energy diversity. They also burn cleanly and thus hold the promise of improved environmental performance.

Currently there is a greatly renewed interest in large scale development of FTS plants to convert coal, biomass and other feed stocks into liquid fuels. While state of the art FTS processes produce a very clean fuel, they also, unfortunately, produce significant emissions of carbon dioxide. This is because coal-derived syngas typically only has $H_2/CO$ ratios in the range of approximately 0.6 to 1.1, dependent on the method of gasification and the ratio of steam to oxygen used to oxidize the coal or other feedstocks in the gasification unit.

State of the art FTS technology relies on the water-gas shift (WGS) reaction to raise the hydrogen to carbon monoxide molar ratio ($H_2/CO$) of the syngas to values of 2.0 or higher that are needed for the FTS process. This, unfortunately, produces one $CO_2$ molecule for each $H_2$ molecule added to the syngas. Unless the $CO_2$ produced by the FTS process is captured and stored, for example, underground, state of the art FTS processes add large amounts of $CO_2$ to the atmosphere, thereby increasing the greenhouse effect. Currently, the only way to prevent this undesirable result is to capture and store the carbon dioxide. Systems for the capture and storage of carbon dioxide, including proposed underground storage systems, are, unfortunately, quite expensive, largely untested, and add significant cost to the synthetic fuel production process.

The present invention relates to a modified and improved FTS process wherein the carbon byproduct produced by the FTS process is in the form of potentially valuable carbon multi-walled nanotubes (MWNT) instead of environmentally troubling carbon dioxide. Thus, the present invention represents a significant advance in the art allowing for the more efficient, effective, economical and environmentally friendly manufacture of synthetic fuels as an alternative fuel supply.

SUMMARY OF THE INVENTION

In accordance with the purposes of the present invention as described herein, an improved method is provided of producing liquid fuels. That method comprises the steps of gasifying a starting material selected from a group consisting of coal, biomass, carbon nanotubes and mixtures thereof to produce a syngas, subjecting that syngas to Fischer-Tropsch synthesis (FTS) to produce a hydrocarbon product stream, separating that hydrocarbon product stream into gaseous $C_1$-$C_4$ hydrocarbons and $C_{5+}$ hydrocarbons used as liquid fuels and subjecting the $C_1$-$C_4$ hydrocarbons to catalytic de-hydrogenation to produce hydrogen and carbon nanotubes, which are in the form of multi-walled nanotubes (MWNT).

In accordance with yet another aspect of the present invention, a liquid fuel production facility is provided. The liquid fuel production facility comprises: (1) a gasification unit to produce a syngas from a starting material selected from a group consisting of coal, biomass, carbon nanotubes and mixtures thereof, (2) a Fischer-Tropsch synthesis (FTS) unit downstream from said gasification unit to produce a hydrocarbon product stream from said syngas, (3) an optional separation unit downstream from said Fischer-Tropsch unit to separate the hydrocarbon product stream into $C_1$-$C_4$ hydrocarbons and $C_{5+}$ hyrdrocarbons used as liquid fuels, (4) a catalytic dehydrogenation (CDH) unit downstream from the separator unit to produce hydrogen gas and carbon nanotubes from the $C_1$-$C_4$ hydrocarbons, and (5) a mixing unit to mix the hydrogen from the CDH unit with the syngas from the CDH unit with the incident syngas from the gasification unit.

In the following description there is shown and described several different embodiments of the invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention and together with the description serve to explain certain principles of the invention. In the drawings.

Reference will now be made in detail to the present preferred embodiment of the invention, examples of which are illustrated in the accompanying drawings.

DETAILED DESCRIPTION OF THE PREFERRED EMBODIMENTS OF THE INVENTION

Figure 1:
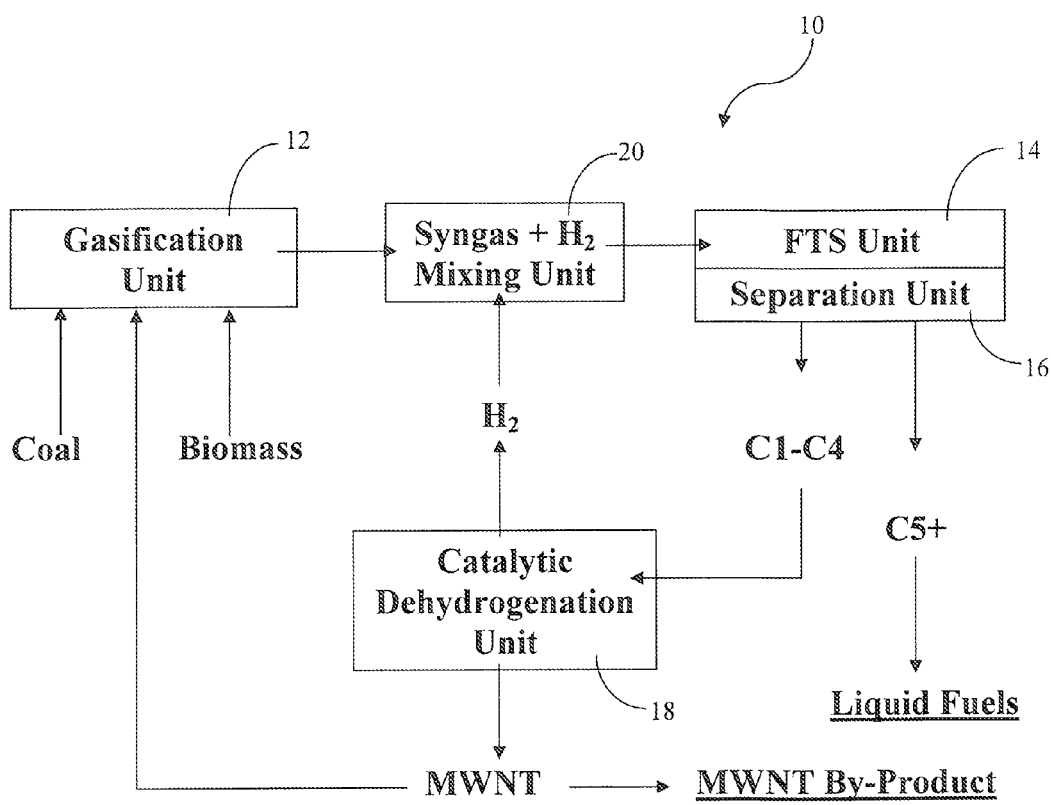
FIG. 1 is a schematic block diagram illustrating the liquid fuel production facility of the present invention.

Reference is now made to FIG. 1 schematically illustrating a liquid fuel production facility 10 for performing the method of the present invention. The liquid fuel production facility 10 comprises: (a) a gasification unit 12, (b) a Fischer-Tropsch Synthesis (FTS) unit 14 downstream from the gasification unit 12, (c) an optional hydrocarbon separation unit 16 downstream from the FTS unit 14, (d) a catalytic dehydrogenation unit 18 downstream from the FTS unit or optional separation unit and (e) a mixing unit 20 downstream from the gasification unit and the catalytic dehydrogenation unit. The optional hydrocarbon separation unit 16 is provided when appropriate hydrocarbon separation is not completed within the FTS unit.

More specifically, feed stock including coal, biomass, carbon nanotubes and mixtures thereof is fed into the gasification unit 12 where the feed stock or starting material is gasified at a relatively high temperature and pressure to produce a syngas or synthesis gas including carbon monoxide and hydrogen. The syngas is then delivered to the FTS unit 14 where the syngas is subjected to FTS processing to produce a hydrocarbon product stream. That hydrocarbon product stream is separated into $C_1$-$C_4$ hydrocarbons and $C_{5+}$ hydrocarbons either in the FTS unit 14 or an optional separation unit 16. The $C_{5+}$ hydrocarbons are then processed into liquid fuels such as gasoline, diesel fuel and jet fuel. In contrast, the $C_1$-$C_4$ hydrocarbon product stream is delivered to the catalytic dehydrogenation unit 18 where it is subjected to catalytic dehydrogenation to produce hydrogen and carbon nanotubes, which are in the form of multi-walled nanotubes (MWNT). Advantageously, the hydrogen is added to the syngas in the mixing unit 20 in order to increase the $H_2$/CO ratio to desired levels for FTS processing while a first portion of the carbon nanotubes is used as a feedstock and a second portion is sold on the market and used to create other products.

Any known method of gasification may be used in the present method. However, methods of gasification that produce a $H_2$—CO ratio for the coal-derived syngas of 0.8 to 1.0 or higher are preferred. Of course, it is known in the art that the ratio may vary greatly from, for example, 0.5 to 1.5, depending on the oxidizing gas used to convert the coal to syngas and the type of gasification reactor. Normally, the oxidizing gas is a mixture of oxygen or air and steam. Higher steam content tends to enhance the hydrogen content of the syngas.

The current method may also use any known method for FTS processing. Currently, the fixed-bed tubular reactor (FBTR) is favored by Sasol, the South African company that leads the world in the commercial development of FTS liquid transportation fuel production. No matter which FTS processing method is used, it is beneficial to complete the FTS processing at temperatures of approximately 200-300° C. using a Co-based FTS catalyst in order to produce fairly high yields of $C_1$-$C_4$ product. The use of an Fe-based FTS catalyst is not favored since Fe is an excellent water-gas shift (WGS) catalyst, a reaction which produces large quantities of carbon dioxide The separation of the $C_1$-$C_4$ product stream from the $C_{5+}$ product stream may be accomplished by distillation processes of a type well known in the art and currently used extensively by all oil refining companies.

With respect to catalytic dehydrogenation of the $C_1$-$C_4$ production stream, substantially any catalytic dehydrogenation process known in the art may be utilized. One particularly useful catalytic dehydrogenation (CDH) process is disclosed in issued U.S. Pat. No. 6,875,417, the full disclosure of which is incorporated herein by reference. This catalytic dehydrogenation process includes the step of passing the $C_1$-$C_4$ hydrocarbons over a catalyst comprising a binary Fe-based alloy catalyst on one of several types of supports. Supports that have been utilized to date include $\gamma$-$Al_2O_3$, a basic support—Mg(Al)O, and carbon nanotubes. Currently, a basic support is favored because cleaning the carbon nanotubes is more easily accomplished due to the fact that basic supports are easily dissolved in a dilute acid solution.

A binary metal-ferrihydrite structure comprising iron and a secondary element M selected from a group of metals consisting of Ni, Mo, Pd, Mn, and any mixtures thereof, are deposited on the support by an incipient wetness method wherein the iron and the secondary metal M present in approximately a composition of 2 to 3 parts Fe and 1 part M and are included in a ratio of between about 5.0 to 20.0 weight percent with respect to the oxide support substrate. In their active state, the Fe-M catalysts are reduced either in hydrogen or syngas to an austenitic metal alloy. Typically, processing temperatures range from about 400° C. to about 900° C. with a preferred temperature range of about 600 to 800° C.

It should be appreciated that the method of the present invention may also include the step of recycling some of the carbon nanotubes produced by catalytic dehydrogenation back to the gasifier and using those as feed stock or starting material to replace some of the coal. Generally, the starting material used in the process comprises between about 80 and about 90 weight percent coal between about 10 and about 20 weight percent carbon nanotubes and between about 10 and about 20 weight percent biomass. Types of coal useful in the present invention include, but are not limited to, lignite, sub-bituminous, bituminous and anthracite. Biomass materials useful as a starting material or feed stock in the present process may be selected from a group of materials including but not limited to wood wastes, agricultural waste materials, and switchgrass.

Numerous benefits result from employing the concepts of the present invention. It is estimated that a 50,000 bbl/day liquid fuel production facility constructed in accordance with the teachings of the present invention would yield approximately 2,315 tons of multi-walled carbon nanotubes per day. The multi-walled carbon nanotube byproduct of the process may be sold on the market or recycled as a feed stock or starting material for the process. If only 10% of the multi-walled carbon nanotubes produced by the present process are sold at $0.25 per pound and the remainder are recycled to the gasifier as a feed stock replacing part of the coal, the added plant revenue would be approximately $200,000.00 per day. Advantageously, the converting of the carbon byproduct of the process to multi-walled carbon nanotubes avoids emissions of approximately 14,350 tons/day (5,237,750 tons/yr) of $CO_2$ and prevents the use of approximately 5,900 tons of water per day (2,153,500 tons/yr) for the water-gas shift (WGS) reaction used to produce hydrogen in prior art FTS processes.

Figure 2A:
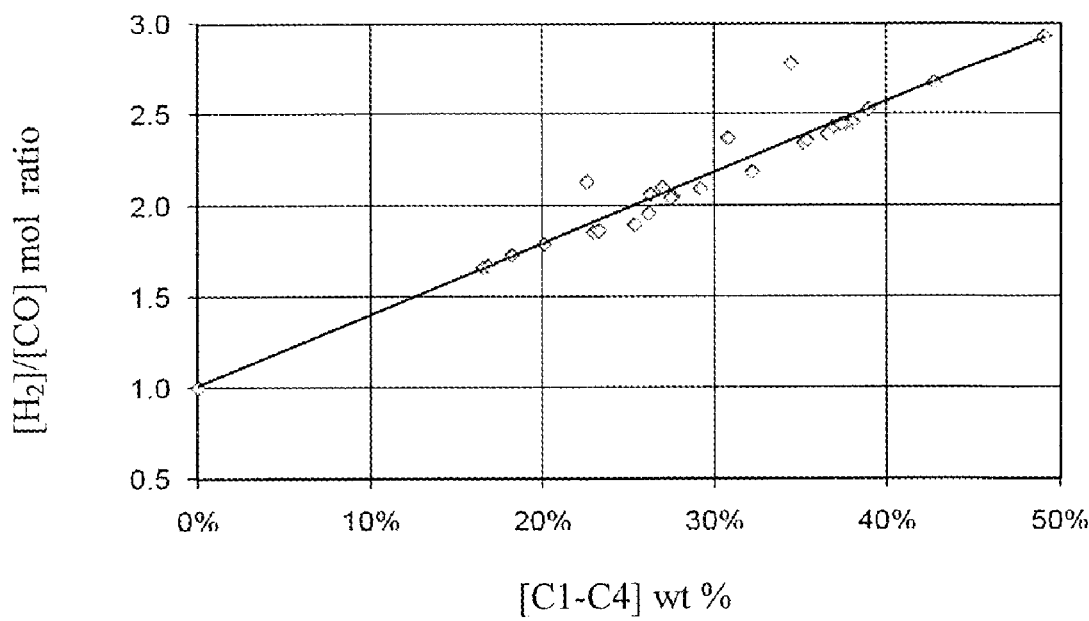
FIGS. 2a and 2b are plots of the [$H_2$]/[CO] ratio of the modified syngas entering the FTS reactor versus the [C1-C4] wt % for two different initial [$H_2$]/[CO] ratios from the gasification unit.
Figure 2B:
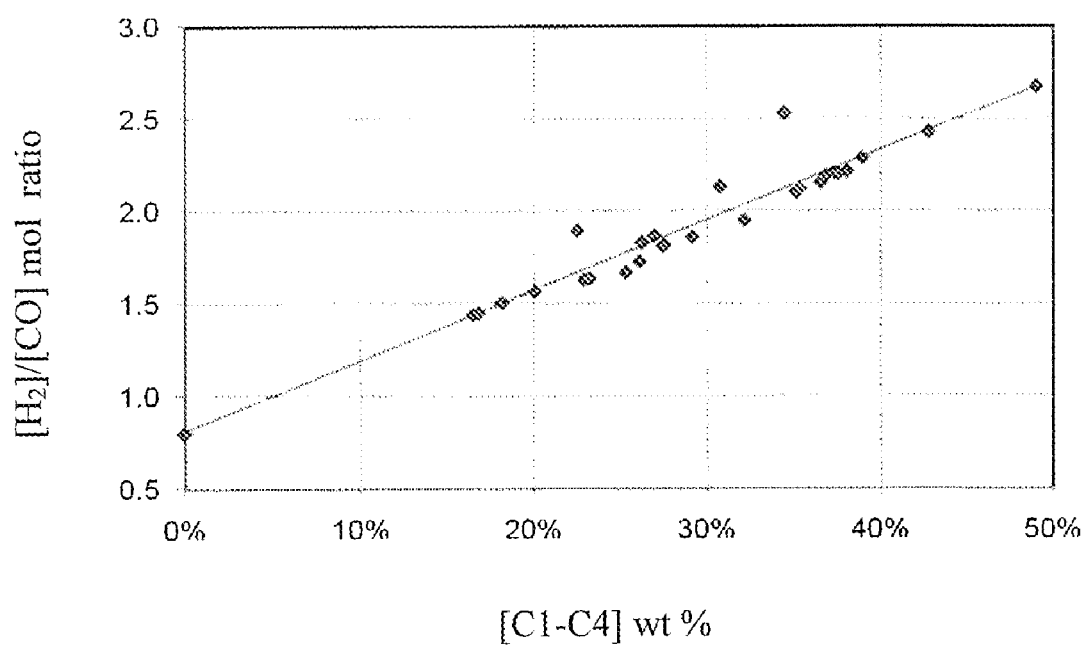

Table 1 (below) and FIGS. 2a and 2b show the [$H_2$]/[CO] ratios obtained by this approach for 54 different examples using Fischer-Tropsch data. It is seen that for 32 of the 54 examples (approximately 60%), the [$H_2$]/[CO] ratios were raised to 2 or higher, achieving the goal required for FT synthesis of liquid fuels. Nearly all of the remaining samples achieved [$H_2$]/[CO] ratios above 1.5; assuming the $H_2$ still required by these samples were produced by the WGS reaction, this would still represent a decrease in $CO_2$ emissions and water use of about half of that calculated above.

TABLE 1

A sampling of 27 FTS data sets showing the wt % of the amounts of $H_2$ ($\Delta H_2$(wt %)) and C MWNT ($\Delta C_M$(wt %)) produced by CDH and the resulting $[H_2]/[CO]$ ratios of the modified syngas. The last column shows the average values from all 27 data sets.

| [C1-C4] wt % | 16.50% | 18.20% | 32.20% | 30.80% | 39.00% | 49.00% | 30.19% |
|---|---|---|---|---|---|---|---|
| $\Delta H_2$(wt %) | 3.91% | 4.29% | 6.81% | 7.80% | 8.62% | 10.61% | 6.82% |
| $\Delta C_M$(wt %) | 12.59% | 13.91% | 25.39% | 28.80% | 30.38% | 38.39% | 24.38% |
| $\Delta C_M$(wt %)/$\Delta H_2$(wt %) | 3.22 | 3.24 | 3.73 | 3.70 | 3.52 | 3.62 | 3.56 |
| *$[H_2]/[CO]$ mol ratio | 1.66 | 1.72 | 2.18 | 2.37 | 2.53 | 2.93 | 2.19 |
| **$[H_2]/[CO]$ mol ratio | 1.44 | 1.50 | 1.95 | 2.13 | 2.28 | 2.67 | 1.96 |

*Initial value = 1.0;
**Initial value = 0.8

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed:

1. A method of producing liquid fuels, comprising:
   gasifying a starting material selected from a group consisting of coal, biomass, carbon nanotubes and mixtures thereof to produce a syngas;
   subjecting said syngas to Fischer-Tropsch synthesis (FTS) to produce a hydrocarbon product stream;
   separating said hydrocarbon product stream into $C_1$-$C_4$ hydrocarbons and $C_5$+ hydrocarbons used as liquid fuels;
   subjecting said $C_1$-$C_4$ hydrocarbons to catalytic dehydrogenation to produce hydrogen and carbon nanotubes; and
   recycling said hydrogen to mix with the syngas produced in the gasifier to yield a syngas with a hydrogen to carbon monoxide ratio of 2 or higher, for FTS of liquid fuels.

2. The method of claim 1 including recycling some of said carbon nanotubes produced by catalytic dehydrogenation as said starting material and adding said hydrogen produced by catalytic dehydrogenation of the $C_1$-$C_4$ hydrocarbons to said syngas prior to Fischer-Tropsch synthesis.

3. The method of claim 1 including using a starting material comprising between about 80 and about 90 weight percent coal, between about 10 and about 20 weight percent biomass and between about 10 and about 20 weight percent carbon nanotubes.

4. The method of claim 1 including selecting said biomass from a group of materials consisting of wood wastes, agricultural wastes, and switchgrass.

5. The method of claim 1, including using multiwalled carbon nanotubes.

6. The method of claim 1, further including producing a syngas with a $H_2$ to CO ratio of 0.8 to 1.0 during said gasifying step.

7. The method of claim 1, wherein said syngas is subjected to temperatures of about 200 to about 300° C. in the presence of a Fischer-Tropsch synthesis catalyst.

8. The method of claim 1, wherein said separating is accomplished by performing distillation.

9. The method of claim 1, wherein said catalytic dehydrogenation includes passing said $C_1$-$C_4$ hydrocarbons over a catalyst comprising an austenitic Fe-M alloy derived from a binary metal-ferrihydrite structure comprising iron and a secondary element M selected from a group of metals consisting of Ni, Mo, Pd, Mn, and any mixtures thereof.

10. The method of claim 9, further including depositing said catalyst on an oxide support substrate by an incipient wetness wherein the iron and the secondary metal M are present in a composition of approximately 2 to 3 parts Fe and 1 part M and are included in a ratio of between about 5.0 to 20.0 weight percent with respect to the oxide support substrate.

11. The method of claim 10, including reducing said Fe M catalysts in their active state, either in hydrogen or syngas to an austenitic metal alloy.

\* \* \* \* \*